(12) United States Patent
Dietrich et al.

(10) Patent No.: US 7,797,042 B2
(45) Date of Patent: Sep. 14, 2010

(54) DEVICE FOR APPLYING A TRANSCUTANEOUS STIMULUS OR FOR TRANSCUTANEOUS MEASURING OF A PARAMETER

(75) Inventors: Stefan Dietrich, Erlangen (DE); Timo Freitag, Hoechstadt/Aisch (DE)

(73) Assignee: Cerbomed GmbH, Erlangen (DE)

( * ) Notice: Subject to any disclaimer, the term of this patent is extended or adjusted under 35 U.S.C. 154(b) by 720 days.

(21) Appl. No.: 11/750,495

(22) Filed: May 18, 2007

(65) Prior Publication Data

US 2008/0249594 A1    Oct. 9, 2008

(30) Foreign Application Priority Data

May 20, 2006    (DE)    ........................ 10 2006 023 824

(51) Int. Cl.
*A61N 1/18*    (2006.01)
(52) U.S. Cl. ................. 607/2; 607/45; 607/46; 607/55
(58) Field of Classification Search ............ 607/45, 607/46, 55
See application file for complete search history.

(56) References Cited

U.S. PATENT DOCUMENTS

| 4,073,296 A | 2/1978 | McCall |
| 4,267,838 A | 5/1981 | McCall |
| 4,319,584 A | 3/1982 | McCall |
| 5,458,625 A | 10/1995 | Kendall |
| 5,514,175 A | 5/1996 | Kim |
| 6,198,971 B1* | 3/2001 | Leysieffer .................. 607/55 |
| 2003/0195588 A1* | 10/2003 | Fischell et al. ............. 607/55 |
| 2006/0025833 A1* | 2/2006 | Daly ........................... 607/55 |
| 2006/0064139 A1* | 3/2006 | Chung et al. ................ 607/45 |
| 2007/0106344 A1* | 5/2007 | Darley et al. ............... 607/55 |
| 2007/0150027 A1* | 6/2007 | Rogers ....................... 607/55 |
| 2007/0213787 A1* | 9/2007 | Kuzma et al. ............... 607/55 |
| 2008/0097549 A1* | 4/2008 | Colbaugh et al. ........... 607/55 |

FOREIGN PATENT DOCUMENTS

| DE | 102005003735 | 7/2006 |
| WO | 2004000413 | 12/2003 |

* cited by examiner

*Primary Examiner*—Carl H Layno
*Assistant Examiner*—Gary A. Porter, Jr.
(74) *Attorney, Agent, or Firm*—Lucas & Mercanti, LLP (57) ABSTRACT

The apparatus for transcutaneous stimulation or transcutaneous measurement of a parameter is a device which fits wholly within the pinna (external ear) of the vertebrate. In order to fit completely within the pinna, the housing is C-shaped and from each end of the housing is a curved section which has a spring action that holds the apparatus inside the ear. This apparatus has a compact design which allows for nerve stimulation in a particularly efficient, ergonomically favorable and easy manipulation for the patient.

20 Claims, 9 Drawing Sheets

DEVICE FOR APPLYING A TRANSCUTANEOUS STIMULUS OR FOR TRANSCUTANEOUS MEASURING OF A PARAMETER

BACKGROUND OF THE INVENTION

The invention relates to an apparatus for transcutaneous application of a stimulus or for transcutaneous measurement of a parameter on or from the skin surface of a vertebrate, in particular a human.

Apparatuses of this type are in use in particular for therapeutic electrical stimulation of the vagus nerve (nervus vagus) in order to achieve a medical effect. Concerning this, it is known with apparatuses for transcutaneous stimulation of nerves or acupuncture points to exert an influence on the neuroelectrical or other characteristic and thus on the function of the nerves to be stimulated or on the tissue by invasive or non-invasive electrical stimulation of the nerves or of the surrounding tissue using clip systems (similar to a clothes peg) or pin-like systems or with the assistance of small needles which, after connection to a control unit, are additionally stimulated electrically. The aim of such a procedure is usually to elicit somatization alterations such as, for example, stress diminution.

Of particular scientific importance are on the one hand stimulation of nerves and tissues in the region of the ear, especially electrical stimulation of the portions of the vagus nerve located there, or stimulation of tissues and nerves by means of caloric, magnetic or other types of stimulation, and the detection of various physiological, pathophysiological or physical parameters such as, for example, body temperature or oxygen saturation.

The non-invasive stimulation of the vagus nerve, the principal nerve of the parasympathetic nervous system, which leads to skin afference in the region of the external ear, is at present mentioned in a few instances in the scientific literature for diagnostic and therapeutic purposes for neurodegenerative disorders such as Alzheimer's, Parkinsonism or epilepsy, reference being made to Ventureyra ECG: "Transcutaneous vagus nerve stimulation for partial onset seizure therapy", Child's Nerv Syst (2002) 16: 101-102, and to Fallgatter A J, Ehlis A C, Ringel T, Herrmann M: "Age effect on far field potentials from the brain stem after transcutaneous vagus nerve stimulation", Int J Psychophysiol (2005) 56: 37-43, and Fallgatter A J, Neuhauser B, Herrmann M J, Ehlis A C, Wagener A, Scheuerpflug P, Reiners K, Riederer P: "Far field potentials from the brain stem after transcutaneous vagus nerve stimulation", J Neural Transm (2003) 110: 1437-1443. In the study by Ventureyra it is merely suggested that it is possible to apply electrical stimuli to the ear in order thus to treat epileptic seizures. No approaches to a solution for an application apparatuses are indicated. In the studies by Fallgatter et al., a stimulation electrode and a reference electrode are placed on a piece of copper plate which is coated with epoxy resin and attached to the ear with a sticking plaster in order thus likewise to employ electrical stimuli for diagnostic purposes after recording an electroencephalographic signal (measurement of currents in the brain) with a commercially available instrument. Such a self-made apparatus is not suitable for accurate placing of the electrodes on the external ear because it must be attached with adhesive tape and does not simulate the shape of the external ear.

For accurate placing of a sensor or a sensor unit for measuring physiological, pathophysiological or physical parameters or for electrical or other types of stimulation of nerves and tissues on the external ear or in the auditory canal, the following two apparatuses are known:

U.S. Pat. No. 5,458,625 describes an apparatus and a method for stimulating nerve portions, located a short distance under the skin of the external ear, of the vagus nerve for treating stress, pain or for muscle relaxation. The instrument comprises a pair of transcutaneous (acting through the skin) stimulation electrodes. These are designed in the form of clothes peg-like clips and are suitable for attachment to the ear lobe. A stimulating current which appears suitable for nerve stimulation is applied via the clip electrodes.

US 2003/195588 A1 proposes a multimodal nerve stimulator. An apparatus which may comprise various sensors and annular electrodes must be introduced deep into the external auditory canal to the site of action. It is further described herein that portions of the vestibularis nerve which might have positive properties in the treatment in particular of epilepsy and dizziness are stimulated in the external auditory canal. The apparatus additionally provides a constructional shape adapted to the anatomy of the auditory canal.

The following circumstances have proved to be disadvantageous with the previously disclosed solutions mentioned:

The scientific literature mentions—as indicated above—stimulation of the tragus or a defined anatomical portion thereof. The described clothes peg-like clip systems do not make it possible to stimulate nerve portions in the region of the external ear which are relevant to the therapy in particular of depression, epilepsy, cardiac symptoms and further neuropathological disease states. An additional factor is that the relatively high voltages, of 80 volt and more, which are necessary with such clip systems to overcome the resistance of the skin represent a very high risk of injury on application in particular to the tragus or other structures of the external ear.

Described clip systems are not, because of their mechanical retaining properties, suitable for application during a movement of the body. There is the risk that the connections will be broken. This in turn entails a risk of injury to the wearer from the now dangling cable connections, and the risk of damage to the electronics in the stimulation unit, for example from a short-circuit.

The previously disclosed apparatus of a multimodal neurostimulator explicitly describes an earpiece which is suitable only for introduction into the external auditory canal. Even the fabrication of such an in-canal earpiece is associated with great difficulties. It is necessary for this, based on previously disclosed methods, to use an impression material for making an impression of the ear in particular for an individual method of construction in order to be able to simulate as true to detail as possible the anatomical course of the auditory canal. Making such an impression is associated with various risks, in particular of injury to the ear drum and various parts of the skin of the tissue which is very sensitive there. Making an impression is made more difficult in the presence of otological pathologies such as, for example, a ruptured ear drum, and can be undertaken only by a skilled person.

The tissue of the external auditory canal is very susceptible to cutaneous irritation, and on introduction of foreign bodies, for example in the case of a previously disclosed neurostimulator, inflammations and allergies may occur in particular as a long-term effect.

In the case of a non-individual design there is an increased risk of injury to the auditory canal structures through the fit being inaccurate.

According to the document mentioned, only the vestibular nerve is stimulated by the indicated earpiece present in the auditory canal. This nerve is a sub-branch of the vestibular cochlear nerve which has only purely sensory types of fibre.

This makes it possible to exert an influence on the organ of balance of a vertebrate and thus on manifestations of dizziness, nausea or spatial orientation, but not to stimulate further nerves, especially the vagus nerve.

Attachment of sensors to such a piece fitting in the auditory canal and having cutaneous contact with the external auditory canal appears worthwhile. However, the following disadvantages should be mentioned: the cutaneous tissue of the external auditory canal continuously produces cerumen which also has the colloquial name earwax. This secretion is deposited on the surface of the sensors and thus falsifies the results of measurement. In addition, it leads to an extensive and persistent contamination of the sensors, which is likely to have effects on the useful life of such a system. In addition, a lack of connection to the external ear, where numerous parameters can, however, likewise be picked up in an advantageous manner, and to the environment as carrier of additional useful sensory information, is regarded negatively.

Finally, the design of the stimulation electrodes is regarded as disadvantageous. The described previously disclosed solution describes electrode loops placed annularly around the earpiece. However, these have a limited area and do not permit stimulation of a defined area in only one dimension or stimulation of portions of the external ear.

For large-area therapeutic and diagnostic use of the method of transcutaneous nerve stimulation on the ear, and measurement of various parameters, it is desirable to integrate a therapeutic and sensory system in a convenient, safe apparatus which can if possible be individually adapted and can be worn at any time without complication, comfortably and inconspicuously, and is suitable in particular for attachment to or in the external ear.

SUMMARY OF THE INVENTION

The invention is therefore based on the object of designing an apparatus of the type mentioned at the outset so that the desirable specifications just indicated are complied with. The intention is to produce an apparatus for applying sensory and therapeutic systems on or in the ear of a vertebrate which enables particularly efficient and simple stimulation of the portions of nerves located in or on the ear, especially the vagus nerve, and a particularly efficient and simple measurement of various bioparameters and environmental parameters, specifically in a simple and almost invisible manner. The apparatus is to be usable in a manner which is particularly simple and especially safe for the patient, and in particular to be removable from the body where appropriate quickly and safely. It is further intended in this connection to propose an efficient apparatus which enables non-invasive stimulation in particular of portions of the vagus nerve and is very comfortable to wear, and which does not require force over a fabrication or fitting by a skilled person. It is further intended that application of the apparatus be possible at places on an ear where the interfering influence of soiling is potentially small. A further aim is for the design and production method for the apparatus to be simple and reliable and suitable for large-area production. In the case of nerve stimulation, it is aimed to make this efficient, ergonomically favourable and easily manipulable by the patient.

The achievement of this object by the invention is characterized in that the apparatus is designed so that it can be accommodated completely in a pinna, i.e. the external ear, of the vertebrate.

The apparatus preferably has, at least in sections, in particular exclusively, a C-shaped configuration. It may have a housing out of which two curved, preferably wire-shaped sections extend. The two curved, preferably wire-shaped sections can have at their ends a spherical element, these preferably being designed as metal spheres or planar electrodes made of conductive synthetic material or carbon fibres in order to function as electrodes.

The housing may include a unit for generating an electrical stimulus for nerve stimulation, and the two curved, wire-shaped sections can each have in their end region an electrode for applying the stimulus to the skin surface. The housing and the two curved, preferably wire-shaped sections can be designed and disposable in such a way that the electrodes come to rest in the region of or near the tragus. The two curved, preferably wire-shaped sections are advantageously designed and disposable in such a way that they come to rest on the skin surface in the region or above or below the cutaneous afferences of the vagus nerve (nervus vagus).

The housing may also comprise, alternatively or additionally, a unit for measuring a parameter, namely a physiological, a pathophysiological or a physical parameter, and the two curved, wire-shaped sections can be designed as resilient holders.

The housing and/or the curved, preferably wire-shaped sections may consist of deformable material. It is moreover contemplated in a refinement that the housing consists of a combination of two materials, in particular of a flexible and of a rigid material.

A rechargeable battery can be disposed in the apparatus. Finally, the apparatus may have an earphone.

The proposed apparatus thus preferably has at least one solid element which is adapted to the shape and size of the external ear and in which at least one sensor or one sensor unit for measuring physiological, pathophysiological or physical parameters or at least one stimulation electrode and at least one reference electrode or at least one applicator of other types of stimulation come to rest in such a way that the at least one sensor or the at least one stimulation electrode and at least one reference electrode or the at least one applicator of other types of stimulation makes contact with the skin surface of the ear of a vertebrate to measure parameters or for applying an electric current or other types of stimulation after connection to a control unit which is integrated in the solid element or external, or is in other indirect or direct connection to the surroundings. The apparatus is moreover particularly designed or suitable for stimulating the vagus nerve in the region of the external ear.

The solid element of the apparatus preferably consists of a synthetic material which has either rigid or flexible and deformable properties. It can be attached to various points on the external ear, i.e. to the front side, the rear side or to both simultaneously, and to undercut points, recesses and elevations.

The solid element can be preshaped and individually configured. In the first case, it is possible for the wearer of the apparatus to adapt the solid element by shaping, e.g. with input of heat, to the individual circumstances of his external ear. In the second case, the solid element is produced individually after an impression of the ear has been made by a skilled person with an impression material, preferably silicone or alginate, e.g. in a negative-positive method. It is additionally possible to provide for the solid element to be produced in a CAD/CAM method.

For optimal comfort of wearing, and to improve the skin contact of the at least one stimulation electrode and of the at least one reference electrode, and of the at least one sensor, the solid element can consist of a combination of materials. This may be a combination of permanently rigid and permanently flexible synthetic material.

A refinement concerning this provides for the use of permanently rigid synthetic material, in which the electrodes and/or sensors are embedded, in the region on the inside of the tragus. Claw-shaped projections which consist of permanently flexible deformable material and find a grip in the concha and in the superior hemiconcha can leave the ends of the permanently rigid section. The solid element of this refinement may moreover consist either completely of permanently rigid or permanently flexible material.

It is furthermore possible to provide for the use of permanently rigid material, in which the electrodes and/or sensors are embedded, in the region on the inside of the tragus, and to replace the claw-shaped gripping projections by deformable wire-like gripping devices. These may be coated with a different material and have at their ends a spherical or planar-like projection.

Another refinement provides for the solid element filling the whole region of the concha and of the superior hemiconcha.

It is also possible the solid element circular similar to a small earphone as is previously known in music reproduction technology and to place this in the concha. This refinement has as holder a projection which winds around the helix and terminates on the rear side of the external ear. This projection may have a flexible configuration.

In a refinement, at least one stimulation electrode and/or at least one reference electrode are introduced into the solid element for electrostimulation. The electrodes may penetrate the surface of the solid element. They serve as points of contact with the body surface. The points of contact may be formed from metal sphere. They may also be formed by planar surface electrodes. It is furthermore possible for the points of contact to be formed by an element of a material with electrical surface conductivity. A current can be applied to the electrodes via an external control unit, which is not a central subject-matter of this invention.

A refinement provides for replacement of the electrodes by signal emitters for a magnetic, caloric, tactile or other type of stimulation. Signal emitters of other types of stimulation can also be combined with the electrodes or occur together.

It is further provided for the apparatus to have at least one sensor for measuring physiological, pathophysiological or physical or chemical parameters of the wearer of the apparatus or of the environment. Possible examples in this connection are a temperature sensor, a movement sensor, a pulse sensor, a blood pressure sensor, a blood flow sensor, a pulse oximetry sensor or a pH sensor. Sensors which are able to measure various environmental parameters and transmit the results to a control unit are also possible.

On insertion of the earpiece, the electrodes and sensors make contact with the skin surface of the external ear, and sensors are securely fixed in the region of the external ear, and it is thus possible for parts of muscles and nerves located there, especially the vagus nerve, to be stimulated, and for various bioparameters and environmental parameters to be measured.

According to a refinement, a (rechargeable) battery intended to ensure the power supply for so-called active sensors can be accommodated in the solid element.

It is furthermore possible to provide for the apparatus to have connection points for an external control unit. Possible examples in this connection are an appliance worn behind the ear or an appliance carried in the hand for electrical muscle and nerve stimulation.

The solid element can be compatible with a previously known loudspeaker system for acoustic reproduction, e.g. a CD earphone or a hands-free unit.

It is possible to provide for the apparatus to have connection points for an external acoustic signal emitter. Possible examples in this connection are a tinnitus noiser or tinnitus masker which is worn behind the ear. The tinnitus noiser can also be integrated in the apparatus in the sense of the above statements.

Thus, an apparatus in particular for application of various types of stimulation or sensor in the region of the external ear is made possible by the inventive proposal, where a stimulation electrode placed in the external ear, especially on the inside of the tragus, serves for transcutaneous stimulation of the auricular branch of the vagus nerve. It is possible thereby to exert an influence on the function thereof via a stimulation unit, which is not a central subject-matter of this invention. The previously known non-invasive nerve stimulation methods and apparatuses using current serve for peripheral nerve and muscle stimulation in particular for pain therapy (TENS—transcutaneous electrical nerve stimulation), for muscle training (EMS—electrical muscle stimulation) or for electro-acupuncture. None of the apparatuses previously known here is provided and suitable for placing the currents via an application aid according to the invention.

The application apparatus is of great advantage in particular in the therapy of depression and states of fatigue, and epilepsy, cardiac symptoms and others.

Apparatuses for application of types of stimulation in or on the external ear have previously existed, as indicated, only in a few cases in a non-advantageous manner. The invention provides a remedy therefor.

BRIEF DESCRIPTION OF THE DRAWINGS

Exemplary embodiments of the invention are depicted in the drawing, showing in:

FIG. 3 the external ear with indication of the regions suitable for attaching the apparatus of the invention, FIG. 4 diagrammatically the circuit diagram of an apparatus for application of various stimuli to the external ear and for detecting a wide variety of parameters using sensors, FIG. 5a/b in each case an ear piece with corresponding electrodes and sensors diagrammatically and in situ, FIG. 6 an exemplary embodiment of an application apparatus which covers the entire concha, FIG. 7 an exemplary embodiment of a claw-shaped apparatus, FIG. 8 an exemplary embodiment of a solid element by means of wire attachment and FIG. 9 an exemplary embodiment of the apparatus of the invention with a C-shaped or bean-shaped configuration for vagus nerve stimulation.

DETAILED DESCRIPTION OF THE INVENTION

Figure 1:
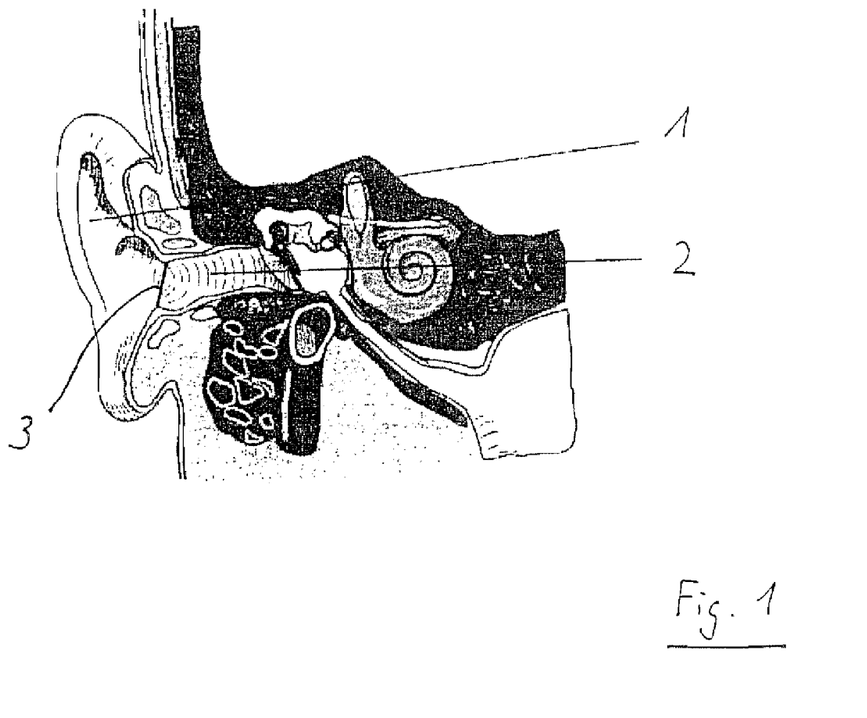
FIG. 1 a sectional view of the anatomical conditions of the external ear.

FIG. 1 gives an anatomical overview for differentiating between the pinna (external ear) and the external auditory canal. The outer ear is composed of two compartments: the external ear 1 and the external auditory canal 2. The anatomical boundary between the two units is the external auditory pore 3, the entrance to the external auditory canal 2.

The external ear has numerous anatomically named portions. For visualization, reference is made here to FIG. 2. In this figure, important anatomical structures of the external ear are defined. These structures become important when the innervation of the external ear is considered. Thus, the tragus 4 or its inner side is the only site on the external ear where portions of the vagus nerve run as auricular branches of the vagus nerve close under the surface of the skin. These nerve portions are suitable for electrical nerve stimulation by an apparatus of the invention for therapeutic and diagnostic purposes.

Figure 2:
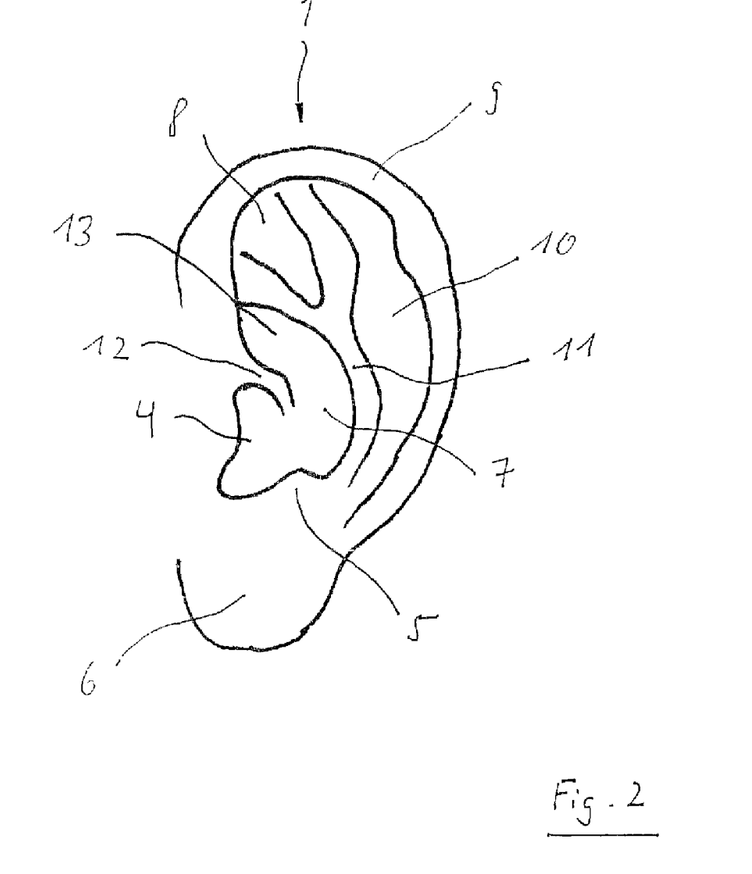
FIG. 2 various anatomical regions of the pinna (external ear)

Indicated and numbered in FIG. 2 are the tragus 4, the antitragus 5, the ear lobe 6, the concha 7, the triangular fossa 8, the helix 9, the scapha 10, the anthelix 11, the crus of helix 12 and the superior hemiconcha 13.

Figure 3:
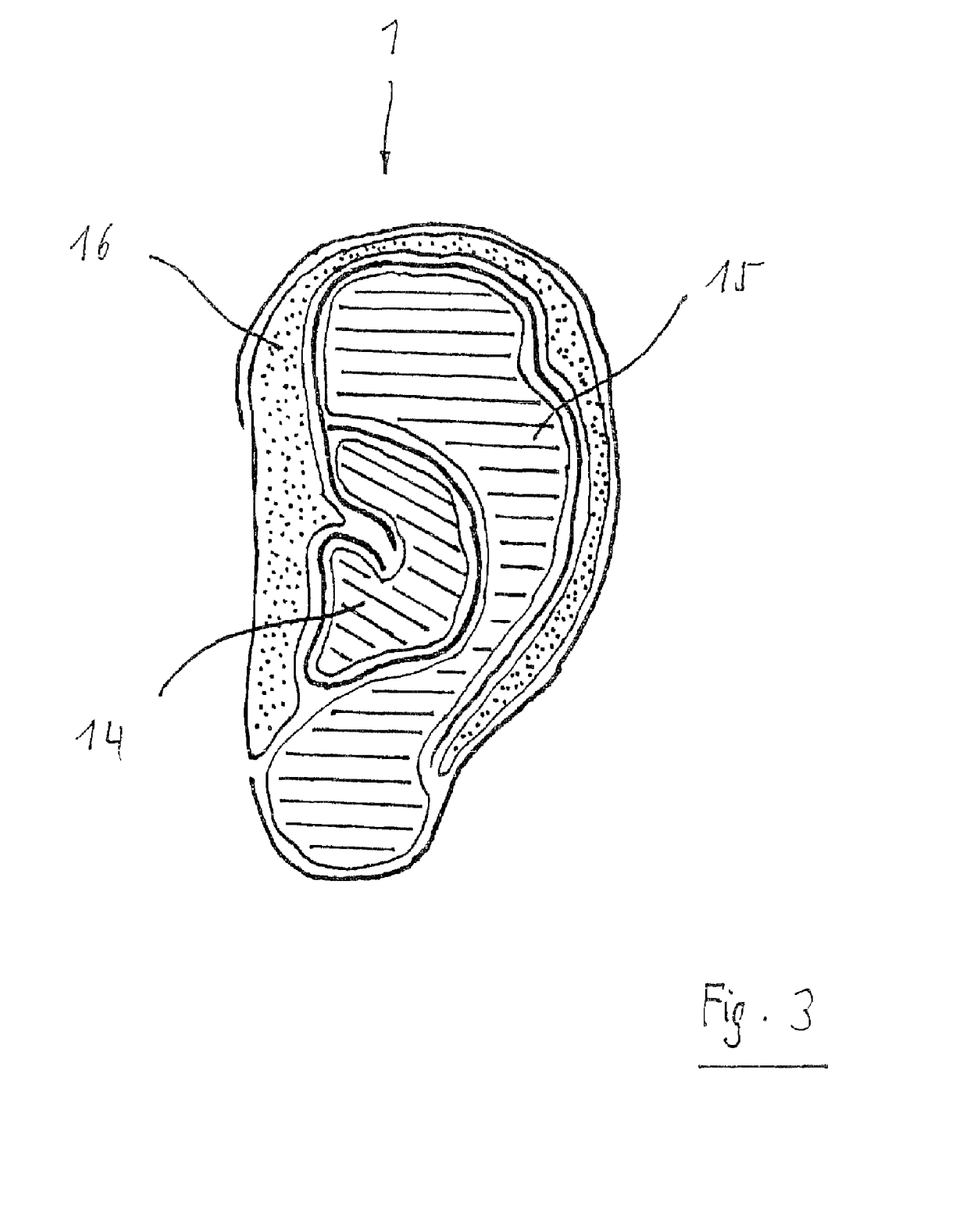

It is evident from FIG. 3 that a large number of the regions of contact of the external ear with the application apparatus are suitable for electrodes and sensors. Reference is made to the shaded and stippled regions 14, 15 and 16 of contact. Regions of contact on the rear side of the external ear are not shown, but are likewise suitable.

Figure 4:
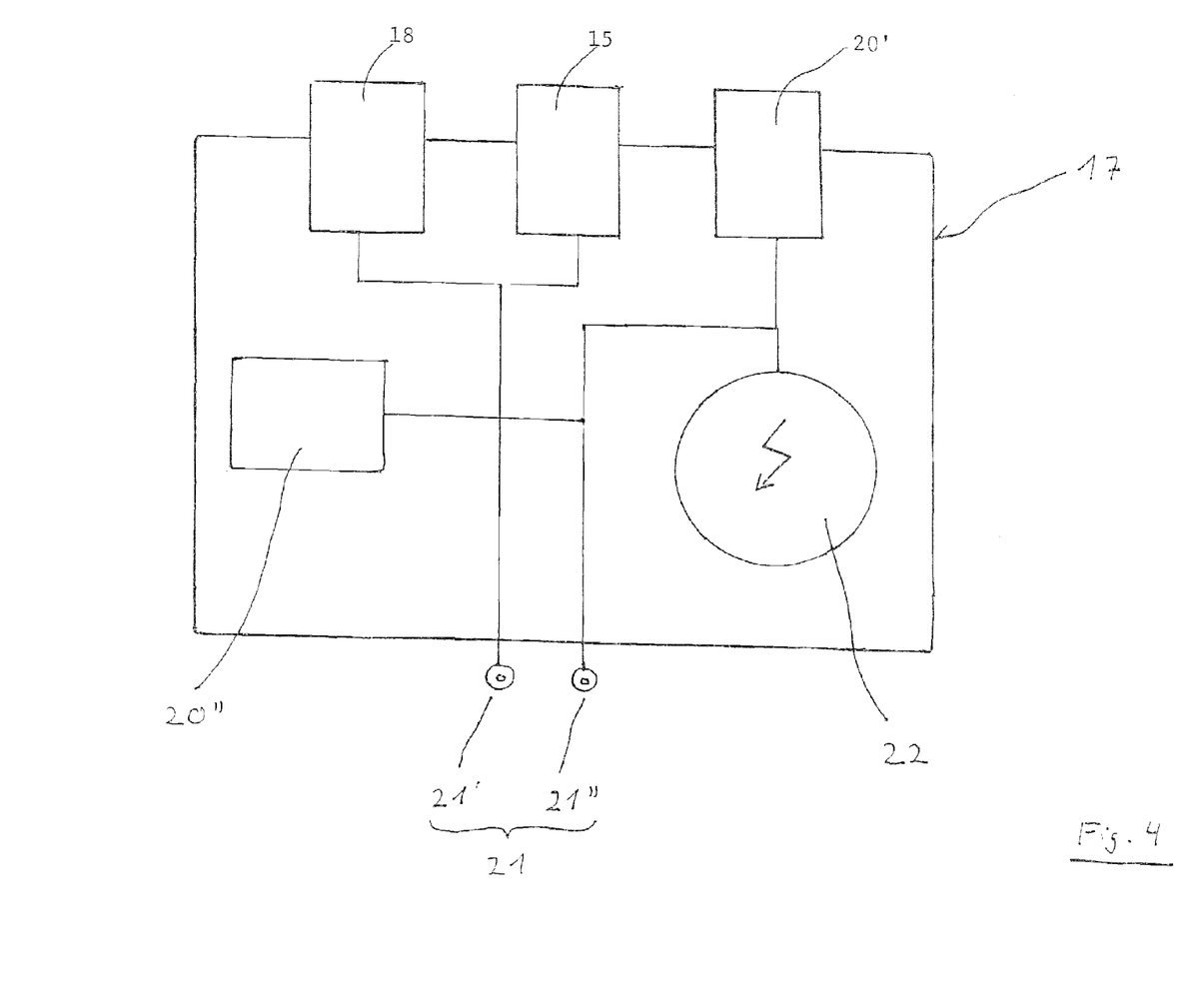

FIG. 4 is a sketch of the circuit diagram of an apparatus 17 for the application of various types of stimulation and sensor in particular for transcutaneous vagus nerve stimulation in the external ear. The apparatus 17 consists basically of at least one stimulation electrode 18 and of at least one reference electrode 19, it also being possible for the reference electrode 19 to be attached outside the apparatus 17. Stimulation of a nerve or tissue takes place via the stimulation electrode 18. The reference electrode 19 serves as electrical reference point. Electrodes for transcutaneous stimulation are known, commercially available and easy to produce. The stimulation parameters can be applied by an external instrument which is connected to the apparatus 17 via a connection unit 21 which can be split into a connection for stimulation electrodes 21' and a connection for sensors 21". Connections of this type are known and universally applicable so that the apparatus 17 can be connected to various external stimulation units. It is also possible to attach specific connections 21' and 21", leading to the apparatus 17 being connectable only to a specific external instrument.

The apparatus 17 further consists of at least one sensor 20' or 20". The sensor 20' has direct contact with the adjacent skin surface. It is thus possible to determine various tissue parameters such as, for example, blood flow rate or blood oxygen saturation. However, the sensor 20' may also have contact with the environment and there determine various parameters such as temperature or humidity. A wide variety of types of sensor are conceivable. Another sensor 20" has no contact with the outside world, but is permanently integrated in the apparatus 17. A wide variety of types of sensors are previously disclosed and commercially available.

The apparatus 17 may additionally comprise a power source 22 in the form of a (rechargeable) battery which, in an advantageous embodiment, can be charged inductively or with solar energy. The power source 22 serves sensors 20' and 20" which require a direct active power supply which is not ensured by a stimulation unit connected from outside.

Figure 5A:
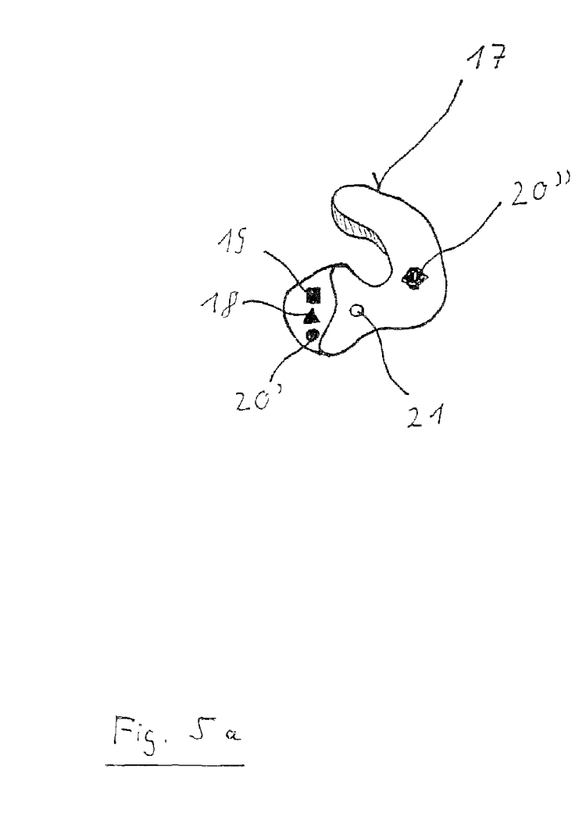
Figure 6:
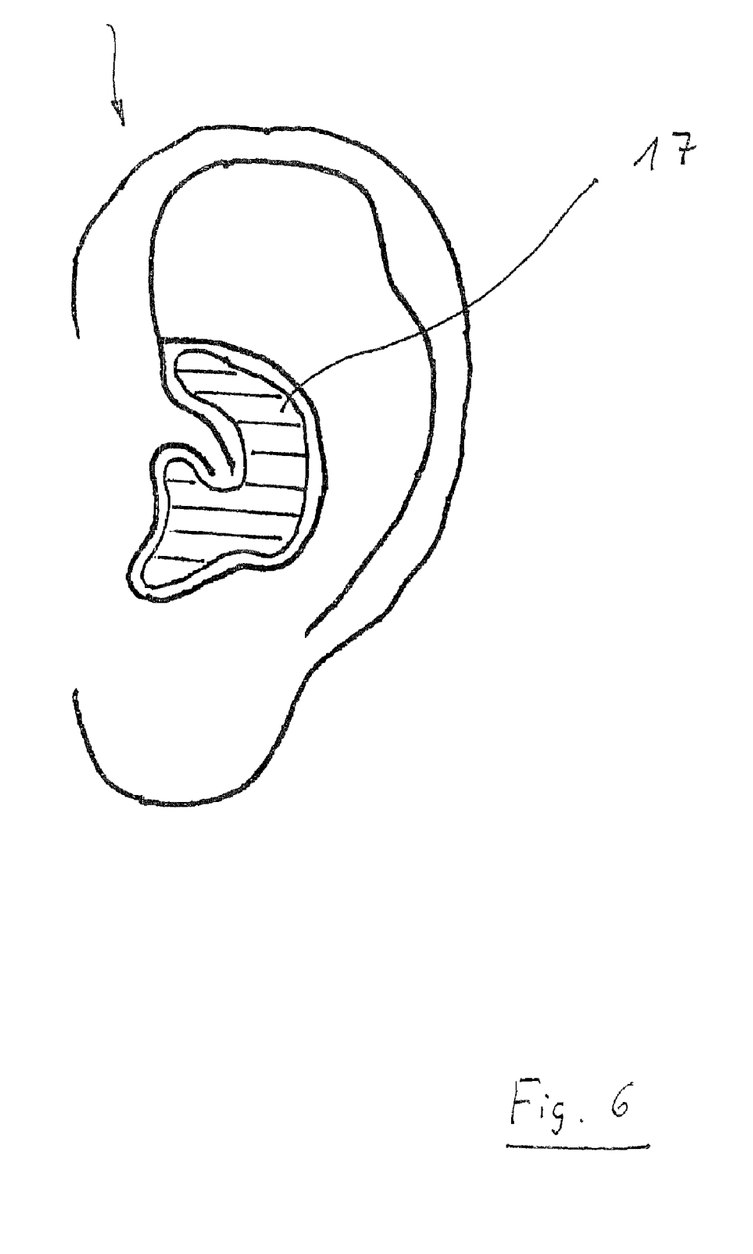

FIG. 5a shows an exemplary embodiment of the apparatus 17 with arrangement of the electrodes 18 and 19, sensors 20' and 20" and the connection 21' or 21". The solid element of apparatus 17 in this case covers, as likewise in the simplified shaded depiction in FIG. 6, the whole region of the concha.

Figure 5B:
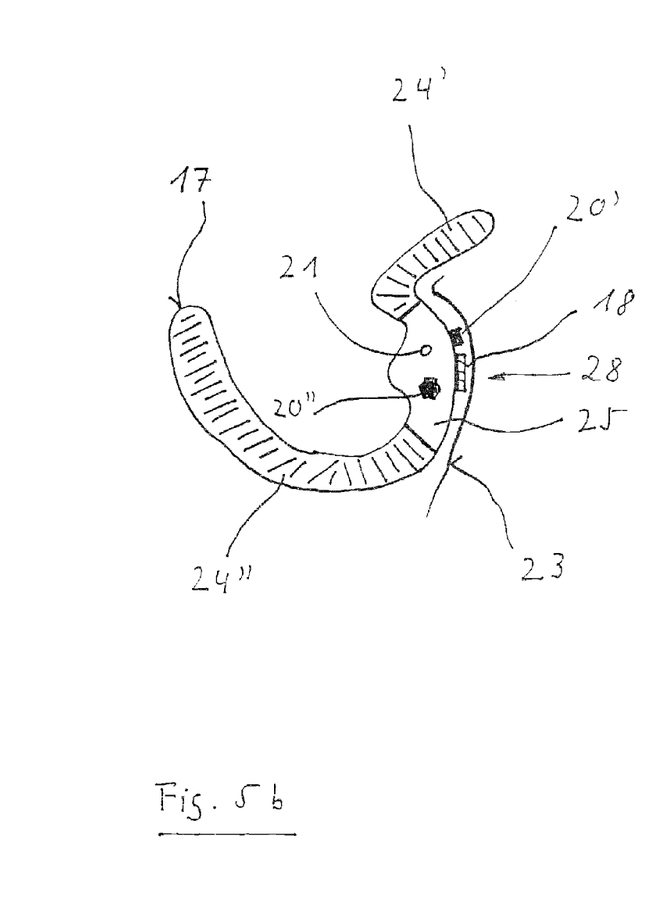
Figure 7:
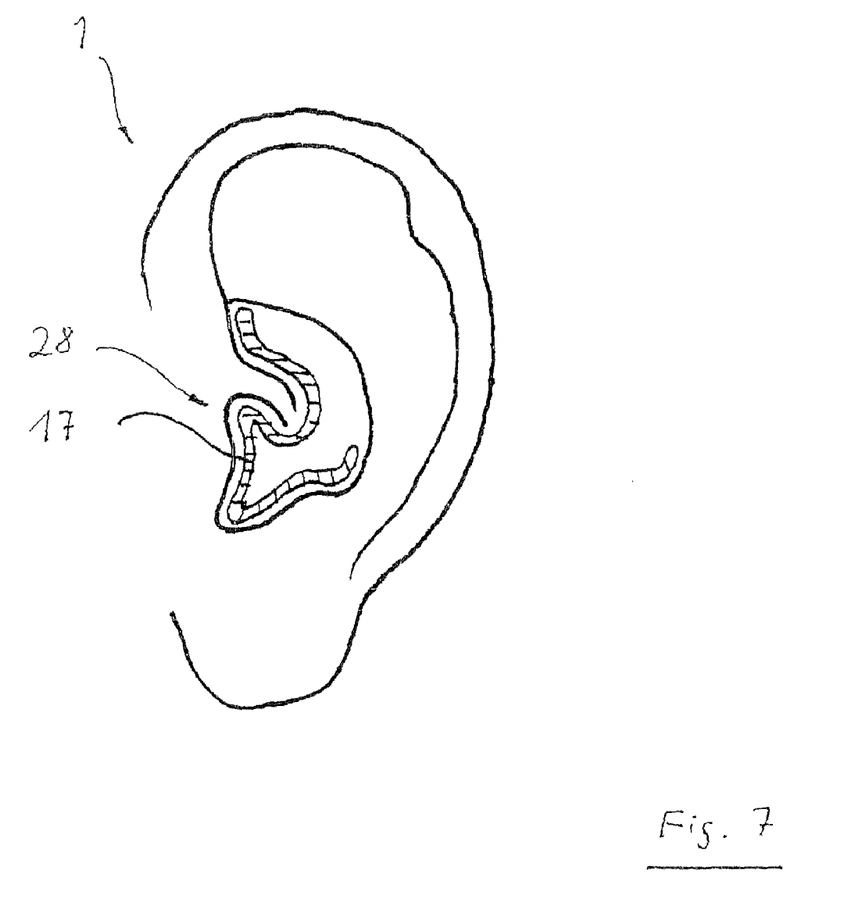

One exemplary embodiment FIG. 5b envisages producing the solid element of the apparatus 17 from two materials which have different strengths and properties. Thus, the unshaded region 25 may consist of a relatively rigid, non-deformable material into which at least the stimulation electrode 18, and the sensors 20' and 20" and a connection unit 21 are inserted. The shaded regions 24' and 24" are preferably formed from a more flexible material which is deformable under certain condition such as, for example, with input of heat. Adaptation to the individual shape of the external ear, in the shown exemplary embodiment FIG. 5b and FIG. 7, to the curvature of the concha 7 and of the superior hemiconcha 13 is thus possible. Individual adaptation by a skilled person is no longer possible in this way. The deformation results in a mechanical tension in the solid element of the apparatus 17, so that the at least one stimulation electrode 18 and the at least one sensor 20' have contact with the skin surface 23. Stimulation by a current applied to the stimulation electrode 18, and measurement of a parameter via a sensor 20' is made possible and ensured thereby. In addition, such a construction results in great comfort of wearing with avoidance of further trips to a skilled person.

Figure 8:
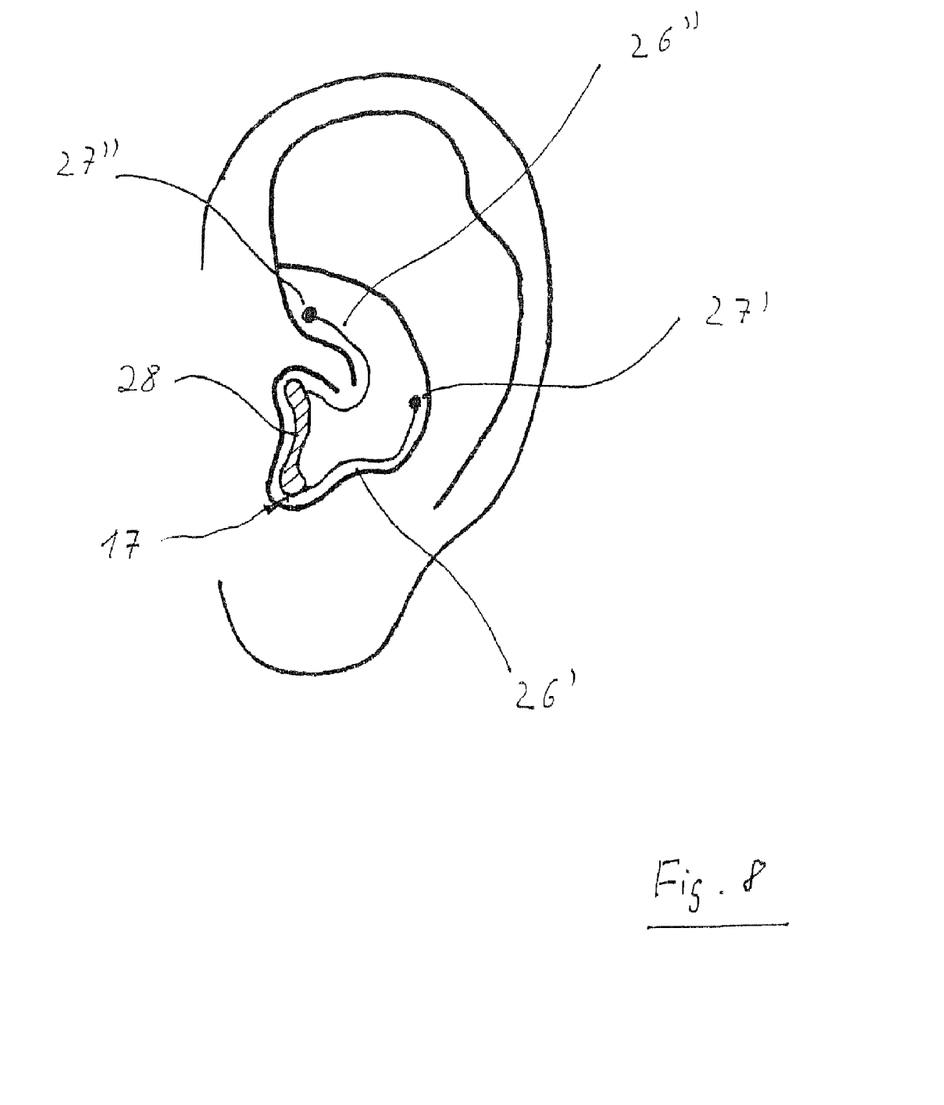

A further exemplary embodiment shown in FIG. 8 provides for replacement of the projections 24' and 24" which are shown shaded in FIG. 5b and are produced from material which remains temporarily flexible by deformable wire elements 26' and 26". Advantages related to manufacture result therefrom, because connecting two synthetic materials with different properties is associated with increased manufacturing costs. The mechanical insertion of deformable wire elements 26' and 26" appears advantageous therefor. The wire elements can be provided with a sheathing for protection. In addition, to prevent injuries and for better manipulation they may have spherical elements 27' and 27" at their ends. In the exemplary embodiment shown in FIG. 8, the stimulation unit is accommodated in the housing 28, with the wire elements 26' and 26" serving merely for holding. In this exemplary embodiment—as in the others too—the housing 28, i.e. the solid element, can be clear of the electronic controls; however, they can also be accommodated therein.

Figure 9:
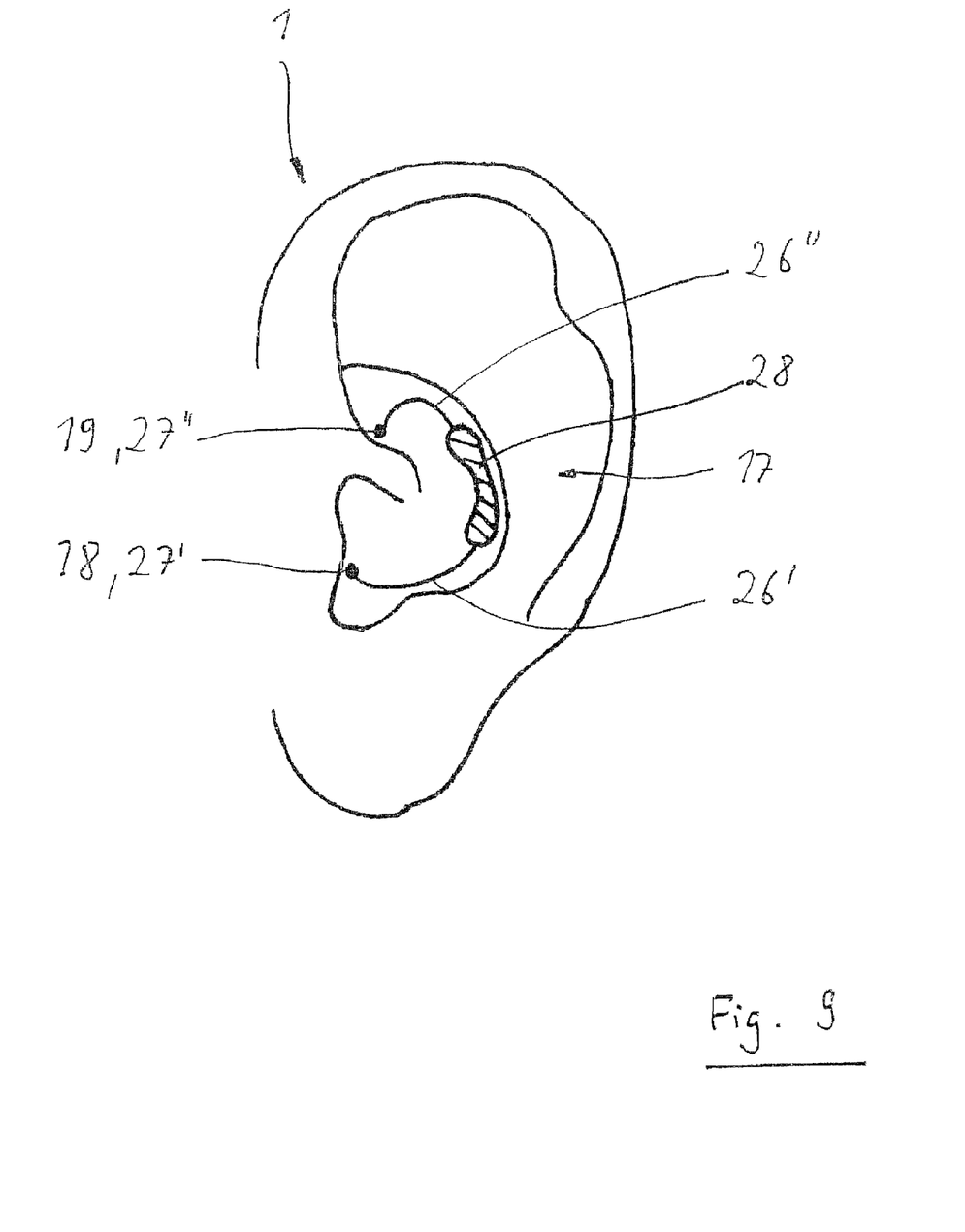

A particularly preferred exemplary embodiment which shows the apparatus 17 for vagus nerve stimulation is evident from FIG. 9. The apparatus for transcutaneous application of an electrical stimulus is completely accommodated in the external ear 1. It has a C-shaped configuration, with a housing 28—i.e. a solid element according to the above terminology—having two curved, wire-shaped sections 26', 26" which extend out of the housing 28. The two wire-shaped sections 26', 26" have at the ends electrodes 18, 19 in the form of metallic spherical elements 27', 27".

In the exemplary embodiment shown in FIG. 9, the stimulation unit is accommodated together with electronic controls and power supply in the bean- or kidney-shaped housing 28, with the wire elements 26' and 26" not serving just for holding here. On the contrary, the power cords to the elements 27', 27' acting as electrodes 18, 19 run therein. The whole apparatus 17 has a C-shaped configuration here.

It is thus possible for the apparatus 17 to be attached easily and completely in the external ear 1, with the wire-shaped sections 26', 26" having a spring action and thus nonpositively or frictionally fixing the complete apparatus 17 satisfactorily in the external ear 1.

The described apparatus can cooperate with a control device. This control device is in one configuration designed as an instrument worn behind the ear. Another solution provides for the control device to be an instrument carried by hand, in which case a wireless connection can be produced between the apparatus in the external ear and the control device.

The invention thus describes an apparatus for applying sensor and therapy systems on or in the ear of a vertebrate, which has at least one solid element which is adapted to the shape and size of the external ear and in which at least one sensor or one sensor unit for measuring physiological, pathophysiological or physical parameters or at least one stimulation electrode and at least one reference electrode or at least one applicator of other types of stimulation, which are capable of delivering a stimulus to the skin surface, come to rest in such a way that the at least one sensor or the at least one stimulation electrode and at least one reference electrode or the at least one applicator of other types of stimulation makes contact with the skin surface of the ear of the vertebrate to measure parameters or for applying an electric current or other types of stimulation after connection to an internal or external control unit or is in other indirect or direct connection to the surroundings.

The inventive proposal makes it possible to apply sensor or therapy systems which can derive their information from or off the skin surface or on the spatial location of the ear of a vertebrate or place different types of stimuli there and are moreover incorporated in or on an individual or non-individual ear insert which comes to rest either in or on the external ear or in or on the external auditory canal, or are attached thereto in another way.

The invention claimed is:

1. An apparatus for transcutaneous stimulation of the skin of a human comprising:
    a housing configured to fit completely in a pinna of the human;
    a stimulation unit, housed within the housing, configured to produce an electronic stimulation signal;
    electronic controls, housed in the housing, configured to control the transcutaneous stimulation;
    a first curved section having a proximal end and a distal end wherein the proximal end of the first curved section is attached to one end of the housing;
    a second curved section having a proximal end and a distal end, wherein the proximal end of the second curved section is attached to the other end of the housing, each of the curved sections having a spring action for securing the housing and the curved sections in the pinna;
    a first electrode mounted at the distal end of the first curved section; and
    a second electrode mounted at the distal end of the second curved section, wherein the first and second electrodes are electrically connected to the electronic controls and are configured to apply stimulation to the skin.

2. The apparatus of claim 1, wherein
the housing has a C-shape.

3. The apparatus of claim 1, wherein
the housing and curved sections have an overall C-shape.

4. The apparatus of claim 1, wherein
the curved sections are made of wire.

5. The apparatus of claim 1, wherein
the electrodes are spherically shaped.

6. The apparatus of claim 1, wherein
the housing and the curved sections are designed so that the electrodes rest in a region of or near a tragus.

7. The apparatus of claim 6, wherein
the curved sections are designed to rest on the skin above the vagus nerve.

8. The apparatus of claim 1, wherein
the housing and the curved sections consist of deformable material.

9. The apparatus of claim 1, wherein
the housing consists of a combination of two materials.

10. The apparatus of claim 1, wherein
the electronic controls include a rechargeable battery.

11. The apparatus of claim 1, further comprising:
an ear phone mounted on the housing.

12. An apparatus for transcutaneous measurement of a parameter from the skin of a human comprising:
    a housing configured to fit completely in a pinna of the human;
    a sensing unit, housed within the housing, configured to measure a physiological, a pathophysiological or a physical parameter;
    electronic controls, housed in the housing, configured to control the measuring of the parameters;
    a first curved section having a proximal end and a distal end wherein the proximal end of the first curved section is attached to one end of the housing;
    a second curved section having a proximal end and a distal end, wherein the proximal end of the second curved section is attached to the other end of the housing, each of the curved sections having a spring action for securing the housing and the curved sections in the pinna;
    a first electrode mounted at the distal end of the first curved section; and
    a second electrode mounted at the distal end of the second curved section, wherein the first and second electrodes are electrically connected to the electronic controls and are configured to measure the parameter from the skin.

13. The apparatus of claim 12, wherein
the housing has a C-shape.

14. The apparatus of claim 12, wherein
the housing and curved sections have an overall C-shape.

15. The apparatus of claim 12, wherein
the curved sections are made of wire.

16. The apparatus of claim 12, wherein
the electrodes are spherically shaped.

17. The apparatus of claim 12, wherein
the housing and the curved sections consist of deformable material.

18. The apparatus of claim 12, wherein
the housing consists of a combination of two materials.

19. The apparatus of claim 12, wherein
the electronic controls include a rechargeable battery.

20. The apparatus of claim 12, further comprising:
an ear phone mounted on the housing.

* * * * *